US012721919B2

(12) United States Patent
Hust

(10) Patent No.: US 12,721,919 B2
(45) Date of Patent: Sep. 1, 2026

(54) METHODS AND REACTORS FOR CREATING A SAFE ANTIMICROBIAL BARRIER ON SURFACES

(71) Applicant: Viridis BioDefense LLC, Dexter, MO (US)

(72) Inventor: Robert Michael Hust, Coeur d'Alene, ID (US)

(73) Assignee: Viridis BioDefense LLC, Dexter, MO (US)

( * ) Notice: Subject to any disclaimer, the term of this patent is extended or adjusted under 35 U.S.C. 154(b) by 1171 days.

(21) Appl. No.: 17/455,525

(22) Filed: Nov. 18, 2021

(65) Prior Publication Data

US 2022/0152257 A1 May 19, 2022

Related U.S. Application Data

(60) Provisional application No. 63/115,195, filed on Nov. 18, 2020.

(51) Int. Cl.

| | |
|---|---|
| ***A61L 2/26*** | (2006.01) |
| ***A01N 25/04*** | (2006.01) |
| ***A01N 25/18*** | (2006.01) |
| ***A61L 2/18*** | (2026.01) |
| ***A61L 2/22*** | (2006.01) |

(52) U.S. Cl.

CPC ................ *A61L 2/26* (2013.01); *A01N 25/04* (2013.01); *A01N 25/18* (2013.01); *A61L 2/18* (2013.01); *A61L 2/22* (2013.01); *A61L 2202/11* (2013.01); *A61L 2202/15* (2013.01)

(58) Field of Classification Search

CPC ..... A61L 2/26; A61L 2/18; A61L 2/22; A61L 2202/11; A61L 2202/15; A61L 2/20; A61L 9/037; A01N 25/04; A01N 25/18; A01P 1/00

See application file for complete search history.

(56) References Cited

U.S. PATENT DOCUMENTS

| | | | | |
|---|---|---|---|---|
| 6,290,024 | B1 | 9/2001 | Ehlert | |
| 7,588,646 | B2 | 9/2009 | Sherrel et al. | |
| 10,190,058 | B2 | 1/2019 | Shirazi et al. | |
| 2005/0260138 | A1* | 11/2005 | Flanigan | A61L 9/03 424/45 |
| 2009/0298935 | A1 | 12/2009 | Flanigan et al. | |
| 2009/0321534 | A1 | 12/2009 | Flanigan et al. | |
| 2021/0353801 | A1* | 11/2021 | Weisenberg | B05B 12/081 |
| 2022/0151243 | A1 | 5/2022 | Agnew et al. | |
| 2022/0152257 | A1 | 5/2022 | Hust | |

FOREIGN PATENT DOCUMENTS

| | | | | |
|---|---|---|---|---|
| DE | 102017000110 | A1 * | 7/2018 | A01N 61/00 |
| WO | 2006076033 | A1 | 7/2006 | |

OTHER PUBLICATIONS

Anderson et al., "Comprehensive Analysis of Sorption Enhanced Steam Methane Reforming in a Variable Volume Membrane Reactor", Ind. Eng. Chem. Res., 2017, 56, 7, pp. 1758-1771.

* cited by examiner

*Primary Examiner* — Brendan A Hensel

(74) *Attorney, Agent, or Firm* — Armstrong Teasdale LLP

(57) ABSTRACT

Described herein are methods for producing multiple disinfecting agents from oils and reactors for producing multiple disinfecting agents from oils. Further described herein are methods and reactors for creating a safe antimicrobial barrier on surfaces.

10 Claims, No Drawings

METHODS AND REACTORS FOR CREATING A SAFE ANTIMICROBIAL BARRIER ON SURFACES

CROSS-REFERENCE TO RELATED APPLICATIONS

This application claims priority to U.S. Provisional Application No. 63/115,195 filed Nov. 18, 2020, the contents of which are incorporated herein by reference in their entirety.

FIELD OF THE DISCLOSURE

Described herein are methods for producing multiple disinfecting agents from oils and reactors for producing multiple disinfecting agents from oils.

BACKGROUND OF THE DISCLOSURE

Many natural oils have antimicrobial benefits, ranging from antibacterial to antiviral and sporicidal. It is standard industry practice to distill natural oils and extract a single chemical species that, for any particular oil, represents either the highest yield or most valuable constituent. A byproduct of this practice is exhibited in pyrolytic fumigation where a specific feedstock is pyrolyzed at a specific temperature to produce a specific fumigation agent.

The present disclosure differs from these known industry practices, for example, by recognizing that antimicrobial and sporicidal oils have numerous chemical compounds that can be extracted with varying degrees of effectiveness for a particular target. The present disclosure focuses on extracting multiple, in and some cases many, active chemical species. In combination, these multiple active chemical species have a higher likelihood of disinfection given a target or multiple targets. In some embodiments, this extraction of chemical compounds occurs simultaneously, such that the compounds are immediately available for application.

Fumigation is known as a delivery method to distribute various antimicrobial particles to surfaces. For example, a single donor species known to be safe for human and/or animal consumption can be deposited on hard, soft, and/or edible surfaces. When surfaces are edible, the fumigants act as a preservative. The vaporized fumigant settles in a prophylactic barrier, which provides an invisible and environmentally safe barrier of protection against microbes and spores. This barrier serves to disinfect environments with which the fumigant comes in contact.

The present disclosure further differs from known industry practices, for example, by allowing production of protective layers deposited on target surfaces that are based on multiple disinfecting agents produced from oils.

Described herein are methods for producing multiple disinfecting agents from oils and reactors for producing multiple disinfecting agents from oils. The present disclosure possesses several advantages compared to previous solutions. Specific advantages of the present disclosure include simplicity, versatility, and the non-toxicity of the active agents to vertebrates and most insects. Additional advantages include that the system and method do not require a skilled operator, that the oil used as a feedstock is sourced, in some embodiments, from nearly any natural oil, and that the method amplifies the fumigant's effectiveness by ensuring that multiple species of active agents are employed easily. Still further advantages include that the fumigant is not harmful to electronics, is less visible than other fumigant layers, and is produced, in some embodiments, without high heat that risks ignition.

BRIEF DESCRIPTION OF THE DISCLOSURE

In one embodiment, the present disclosure is directed to a method for producing and providing at least one disinfecting agent, the method comprising: (i) introducing a mixture comprising an oil and a liquid carrier into a container; (ii) transporting the mixture from the container to a reaction zone; (iii) reacting the oil in the reaction zone to produce at least one disinfecting agent; and (iv) providing the at least one disinfecting agent to an application space.

In another embodiment, the present disclosure is directed to a reactor comprising: a container comprising a mixture comprising an oil and a liquid carrier; a power plant; and a reaction zone, wherein the oil reacts in the reaction zone to produce at least one disinfecting agent.

DETAILED DESCRIPTION OF THE DISCLOSURE

The present disclosure relates generally to the production of disinfecting agents from an oil feedstock for fumigation. In many embodiments, multiple disinfecting agents are produced from the oil feedstock. Typically, an oil and liquid carrier are introduced to a reactor having a container and a reaction zone, the oil is transported from the container to the reaction zone, the oil reacts in the reaction zone to produce at least one disinfecting agent, and the at least one disinfecting agent is provided to an application space (e.g. by blowing the at least one disinfecting agent into the application space). The reactor typically has an oil container, a power plant, and a reaction zone.

The system of the present disclosure comprises, in some embodiments, three subsystems: a first subsystem designed for storage of oil; a second subsystem that is a power supply and control unit; and a third subsystem designed for pyrolytic vaporization/volatilization. The system enables the volumization and application of disinfecting agents derived from oils.

In some embodiments, the system comprises a chassis or housing, a container (e.g. storage and/or feeding tank(s)), a power and control module, and at least one pyrolytic vaporization module.

In some embodiments, the system provides at least one disinfecting agent to an application space. In some embodiments, the system fumigates an application space. In some embodiments, the system blows at least one disinfecting agent into an application space. In some embodiments, the system diffuses at least one disinfecting agent into an application space.

Disinfecting Agents

As used herein, disinfecting agent or agents refer to agents that are active against certain living and/or infectious targets.

The disinfecting agents are agents that are extracted from an oil by the methods according to the present disclosure. In some embodiments, the disinfecting agents are known in the art. In some embodiments, the disinfecting agents are newly produced by the methods according to the present disclosure. In some embodiments, the disinfecting agents are a combination of disinfecting agents known in the art and novel disinfecting agents.

The disinfecting agents typically include at least two, at least three, at least four, or at least five disinfecting agents. Numerous disinfecting agents are produced according to the present methods, and dwell times and temperatures are satisfactorily adjusted to achieve efficient and effective extractions.

In some embodiments, the disinfecting agents each individually comprise a functional group selected from the group consisting of long chain fatty acids, long chain fatty alcohols, alcohols, alcohol analogs, phenols, terpenes, terpenoids, aldehydes, carboxylic acids, cyclic ethers, esters, alkyl esters, ketones, and combinations thereof. In some embodiments, the disinfecting agents each individually comprise a functional group selected from the group consisting of long chain fatty acids, long chain fatty alcohols, alcohol analogs, phenols, terpenoids, aldehydes, ketones, and combinations thereof.

In some embodiments, the disinfecting agents comprise a disinfecting agent selected from the group consisting of acetaldehyde, butanal, benzene, pentanal, methyl furan, heptanal, hexanal, decanal, dodecanal, nonanal, butene, propenal, propanal, butylfuran, methyl-tetrahydrofuran, butyl-tetrahydrofuran, methyl propionate, acetic acid, palmitic acid, linoleic acid, linolenic acid, alpha linoleic acid, oleic acid, stearic acid, hexanoic acid, octanoic acid, lauric acid, myristic acid, palmitoleic acid, glycerin, glycerol, ethanol, and combinations thereof.

In some embodiments, the disinfecting agents demonstrate synergistic disinfection activity. In some embodiments, the disinfecting agents demonstrate specific disinfection activity for one target compared to another target.

In many embodiments, the disinfecting agents are used in a consumer product. In some embodiments, the reactor is in the form of a consumer product. Suitable consumer products include products that comprise the disinfecting agents and/or deliver the disinfecting agents to a surface comprising a living and/or infectious target. In some embodiments, the consumer product is a consumer product selected from the group consisting of a fumigant, a nebulizer, a vaporizer, mister, and combinations thereof. As used herein, a fumigant means a vapor, an aerosol, a smoke, a fog, a mist, or a cloud. In some embodiments, the fumigant is visible. In some embodiments, the fumigant is invisible.

Targets

In many embodiments, the disinfecting agents or agents according to the present disclosure are deposited on a target surface. In some embodiments, the target surface is a hard surface, a soft surface, and/or an edible surface.

In some embodiments, the target surface is selected from the group consisting of a counter, a table, a floor, a wall, a ceiling, a toilet, a sink, a shower, a tub, a bedding surface, a food, a machine surface, a hard metal surface, a plastic surface, a wooden surface, furniture, upholstery, draperies, machinery, and combinations thereof.

In many embodiments, the disinfecting agents or agents according to the present disclosure are active against a variety of living and/or infectious targets. In some embodiments, the disinfecting agents or agents according to the present disclosure are active against specific living and/or infectious targets. In some embodiments, the disinfecting agents or agents possess an activity selected from the group consisting of antimicrobial, antiviral, antibacterial, sporicidal, antifungal, and combinations thereof. In some embodiments, the disinfecting agents or agents are active against microbes, viruses, bacteria, spores, fungi, biofilms, and combinations thereof.

In some embodiments, the disinfecting agents or agents are active against a target selected from the group consisting of strains of influenza virus, coronaviruses, SARS-CoV-2 (COVID-19), variants of SARS-CoV-2 (COVID-19), the lineage B.1.1.7 (alpha) variant of SARS-CoV-2, the lineage B.1.351 (beta) variant of SARS-CoV-2, the lineage P.1 (gamma) variant of SARS-CoV-2, the lineage B.1.617.2 (delta) variant of SARS-CoV-2, the lineage C.37 (lambda) variant of SARS-CoV-2, the lineage B.1.621 (mu) variant of SARS-CoV-2, West Nile virus, small pox virus, *Bacillus, Bacillus anthracis, B. lichenformis, B. megaterium, Yersinia, Yersinia pestis, Salmonella, Escherichia, Shigella, Pseudomonas, Serratia, Enterobacter, Clostridium, Clostridium botulinum, Campylobacter, Klebsiella, Mycobacterium, Staphylococcus, Bordetella, Streptococcus, Francisella, Legionella, Vibrio, Blastomyces, Candida, Stachybotrys, Aspergillus, Aspergillus candidus, Aspergillus falus, Acremonium, Histoplasma, Linea, Fusarium, Fusarium solani, Ceratocystis, Cladisporium, Penicillium, Botrytis*, and combinations thereof.

In some embodiments, the disinfecting agents or agents are active against a target selected from the group consisting of strains of *Salmonella, Staphylococcus*, and combinations thereof.

Oil Feedstock

In many embodiments, the oils are selected from any oil feedstock known in the art that is suitable to produce disinfecting agents. Known oils include human consumable vegetable oils and animal oils. Seed oils are particularly advantageous. Oils derived from wood should be avoided because they produce noxious and toxic volatiles and other compounds.

In many embodiments, the oil is a biogenic oil. In many embodiments, the oil is a plant-based or plant-derived oil. In some embodiments, the oil is selected from the group consisting of vegetable oil, alkylated vegetable oil, vegetable oil derivatives, soybean oil, linseed oil, flax oil, safflower oil, mineral oil, corn oil, olive oil, sunflower seed oil, rapeseed oil, biogenic oil, planted-derived oil, plant-based oil, herbaceous oil, waste oil, fryer oil, recycled oil, and combinations thereof.

In some embodiments, the oil is a vegetable oil. In some embodiments, the oil is an oil comprising a constituent comprising a long chain fatty acid.

In some embodiments, the oil is a waste oil. In some embodiments, the oil is a waste oil selected from the group consisting of waste vegetable oils, waste animal oil, waste cooking oils, waste oils from trees, waste oils from fossil fuels, and combinations thereof. Waste cooking oils are particularly useful. Waste oils from trees and fossil fuels are useful but are often more toxic and environmentally harmful than other waste oils.

In many embodiments, one or more oils are used in the methods of the present disclosure. In some embodiments, the oil comprises at least one oil selected from the group consisting of natural oils, processed oils, waste oils, and combinations thereof. In some embodiments, the oil comprises at least two oils selected from the group consisting of natural oils, processed oils, waste oils, and combinations thereof.

Carrier Liquid

In many embodiments, the oil is combined in a mixture with a carrier liquid. In some embodiments, any suitable carrier liquid for vaporization known in the art is useful. Considerations for suitable carrier liquids include flow properties, thermal properties, reaction properties, and cost.

In some embodiments, the carrier liquid is selected from the group consisting of propylene glycol, vegetable glycerin, glycerol, vegetable oil, nut oil, seed oil, wood oil, biodiesel, and combinations thereof.

Reactions

In many embodiments, disinfecting agents produced according to the present disclosure are produced in parallel from the oil through any suitable means of production for such compounds. The means of production are configured for optimal production of multiple disinfecting agents from the oil.

In some embodiments, disinfecting agents are produced from the oil with a technique selected from the group consisting of pyrolytic decomposition, steam distillation, catalytic decomposition, and combinations thereof. Heat-based techniques decompose the oil into one or more reactive constituents in the reaction zone. In some embodiments, these constituents further react with the same or different constituents depending on the chemical environment of the reaction zone or formation of intermediate, metastable phases.

In some embodiments, disinfecting agents are produced from the oil with a catalytic reactor selected from the group consisting of floating catalyst reactors, packed bed reactors, and combinations thereof. In these embodiments, particularly suitable catalysts include noble metals, Cu, $CuO_x$, $CaCO_3$, and non-toxic organometallic catalysts. The residence time of such catalytic reactors should be adjusted to achieve the necessary dwell times to produce multiple disinfecting agents of interest.

Atomization

In some embodiments, the oil is atomized by any suitable method of atomization. In some embodiments, the method step of atomizing comprises an introduction technique selected from the group consisting of spraying the oil, drawing the oil through a Venturi port or nozzle, wicking the oil, film processing, and combinations thereof.

In some embodiments, when the atomization method comprises wicking the oil, the mixture is vaporized via a wick that puts the oil mixture in contact with a heating coil to vaporize the mixture within the heating chamber. In some embodiments, after atomization, forced air is introduced into a heating chamber to blow a vaporized fumigant into the air.

Dwell Time

In many embodiments, the oil is in a reaction zone of the reactor for a dwell time suitable to produce at least two disinfecting agents. In some embodiments, the oil is in a reaction zone of the reactor for a dwell time suitable to produce at least one disinfecting agent. As used herein, dwell time is the time during which the oil is in a reaction zone of the reactor. Dwell times vary between disinfecting agents and the properties of the reactor, such as the oil flow rate, and are satisfactorily adjusted to optimize production of desired disinfecting agents.

In some embodiments, the dwell time is in the range of from about 0.01 seconds to about 2.5 seconds. In some embodiments, the dwell time is less than about 2 seconds. In some embodiments, the dwell time is less than about 1.5 seconds. In some embodiments, the dwell time is less than about 1 second. In some embodiments, the dwell time is less than about 0.5 seconds.

In some embodiments, particularly for film processing, the dwell time is in the range of from about 30 seconds to about 60 seconds for the portion of the oil reacted.

In many embodiments, a gas flow rate is varied to achieve desired dwell times. Specific gas flow rates depend on the reaction kinetics and desired throughput of disinfecting agents.

Temperature

In some embodiments, various components of the reactor are heated. In some embodiments, all components of the reactor are heated. In some embodiments, various components of the reactor are unheated. In some embodiments, all components of the reactor are unheated. Any suitable heating element known in the art (e.g. Nichrome, steel, Inconel, molybdenum disilicide, silicon carbide, etc.) is useful to provide heating.

In some embodiments, when the reaction zone is unheated, it is operated at ambient temperature. In some embodiments, when the reaction zone is unheated, it is operated at a temperature in the range of from about 10° C. to about 40° C. In some embodiments, when the reaction zone is heated, it is operated at a temperature in the range of from about 70° C. to about 1000° C.

In some embodiments, the reaction zone is operated at a temperature in the range of from about 200° C. to about 800° C. In some embodiments, the reaction zone is operated at a temperature in the range of from about 300° C. to about 700° C. In some embodiments, the reaction zone is operated at a temperature in the range of from about 400° C. to about 600° C. In some embodiments, the reaction zone is operated at a temperature in the range of from about 400° C. to about 500° C.

In some particular embodiments, the reaction zone is operated at a temperature in the range of from about 200° C. to about 550° C. In some particular embodiments, the reaction zone is operated at a temperature in the range of from about 390° C.±50° C. Within this temperature range, numerous disinfecting agents become available while avoiding the production of excess solid particles, excess fine particles, and combustion.

Reactor Components

In many embodiments, the reactor comprises several components in a variety of arrangements and orientations to produce multiple disinfecting agents. These components include, but are not limited to, the components described herein.

Reaction Zone

The reactor comprises a reaction zone. In some embodiments, the reaction zone is heated. In some embodiments, the reaction zone is unheated.

In some embodiments, a mixture of an oil and a liquid carrier is transported from a container to a reaction zone. In the reaction zone, the oil within the mixture is reacted to produce at least one disinfecting agent. In some embodiments, the oil is reacted in the reaction zone to produce at least two disinfecting agents.

In some embodiments, the reaction zone comprises a first end comprising a fluid input and a second end comprising a fluid output. In some embodiments, the reaction zone comprises additional fluid outputs, which are located anywhere along its length. In some embodiments, each fluid input is individually configured to allow passage of an oil. In some embodiments, each fluid output is individually configured to allow passage of a gas flow comprising at least one disinfecting agent. In some embodiments, each fluid output is individually configured to allow passage of a separated gas flow comprising at least two disinfecting agents.

In some embodiments, the oil is introduced into a first end comprising a fluid input of the reaction zone.

In some embodiments, the reaction zone comprises a cowling. In some embodiments, gas flow passes through the cowling to increase the number and volume of disinfecting agents capable of being produced.

In some embodiments, the reaction zone comprises a passage element selected from the group consisting of a conduit, a tube, a tunnel, a pipe, a hose, and combinations thereof.

The reaction zone is generally of sufficient size such that exhaust residue, when present (e.g. from combustion), does not hinder the production of disinfecting agents. The size of the reaction zone is large enough to allow significant throughput of disinfecting agents yet small enough to avoid altering the fluid dynamics of the reactor. In some embodiments, the width or diameter of the reaction zone is in the range of from about ⅛ inches to about 3 inches. In some embodiments, the width or diameter of the reaction zone is in the range of from about ½ inches to about 3 inches.

In some embodiments, the reaction zone comprises a material that inhibits buildup of exhaust residue. Any suitable material known to inhibit buildup of exhaust residue is useful. Specifically useful materials include Al/80Ni20Cr alloy, HVOF-sprayed NiCrSiB alloy, 310S type stainless steels, high-Cr Mo—Ni base alloys, and high Si—Cr—Ni—Fe alloys.

Frame

In some embodiments, the reactor comprises a frame that is selected from the group consisting of a chassis, a housing, and combinations thereof. As used herein, a chassis is a mechanical framework that provides structural integrity and holds the other components in place. As used herein, a housing is a mechanical framework that provides structural integrity and holds the other components in place, and also covers components and protects them from wear and damage over the course of use.

In some embodiments, the chassis or housing comprises a material selected from the group consisting of plastic, fiberglass, carbon fiber, metal, and combinations thereof.

In some embodiments, the form factor of the chassis or housing depends on the system's size and use. In some embodiments, the chassis or housing is static or mobile. In some embodiments, the chassis or housing is mobile.

In some embodiments, when the chassis or housing is mobile, the chassis or housing is movable by a person. In some embodiments, when the chassis or housing is mobile, the chassis or housing is in a configuration selected from the group consisting of on wheels, on a motorized conveyance, part of an autonomous vehicle, mounted on a pack-frame, mounted on a hydraulic assisted support frame, handheld, carried by hand, and combinations thereof.

Oil Container

In some embodiments, a container for the oil feedstock is coupled to the chassis or housing with a mechanical coupler. In some embodiments, the container is open, closed, or sealed. The size of the container depends on the desired throughput. In some embodiments, the coupling is permanent, semi-permanent, or temporary. Suitable mechanical couplers include grommets, hooks, buttons, snaps, clips, clamps, and bolts.

In some embodiments, the container does not comprise a gravity feed. In some embodiments, the container comprises sensors that determine a fumigant level. In some embodiments, the container comprises a pump.

In some embodiments, the chassis or housing comprises more than one container. In some embodiments, the containers are sufficient in size and number to provide enough fumigant mixture to accomplish a given scale of fumigation.

In some embodiments, the application space is relatively small, such as a small room. In some embodiments, the container carries an amount of oil on the scale of ounces.

In some embodiments, the application space is relatively large, such as a warehouse or hangar. In some embodiments, the container carries an amount of oil on the scale of gallons.

In some embodiments, the application space is relatively large and open, such as a space measured in acres. In some embodiments, the container carries an amount of oil on the scale of hundreds of gallons.

Gas and Fluid Pumps

In some embodiments, a gas pump is fluidically connected to both the oil container and reaction zone via a fluidic coupling. In some embodiments, a gas pump is fluidically connected to both the oil container and reaction zone via a fluidic coupling selected from the group consisting of a tube, a pipe, a cylinder, and combinations thereof. In some embodiments, the gas pump is an air pump.

In some embodiments, a fluidic pump is used to transmit the oil mixture into and through the reaction zone. In some embodiments, the fluidic pump is selected from the group consisting of peristaltic pumps, positive displacement pumps, syringe pumps, and cylinder pumps.

In some embodiments, a mixture comprising an oil and a liquid carrier is transported from the container to a reaction zone.

Power Plant

In some embodiments, a power plant is mechanically coupled to the chassis or housing with a mechanical coupler. The power plant drives gas flow and heat, along with a gas-oil mixture into the reaction zone. In some embodiments, the power plant is a power plant selected from the group consisting of electrical power plants, combustion engine power plants, and combinations thereof.

In some embodiments, the electrical power plant is in a form selected from the group consisting of an electric motor, a battery, and combinations thereof.

In some embodiments, the electrical power plant comprises a heat source selected from the group consisting of an induction coil, a plasma mechanism, and combinations thereof. In some embodiments, the heat source drives a component selected from the group consisting of a gas pump, a fan, a jet, and combinations thereof. In some embodiments, the electrical power plant comprises an induction coil that is mechanically coupled to the reaction zone.

In some embodiments, the electrical power plant comprises a distal element. In some embodiments, the electrical power plant comprises a distal element selected from the group consisting of a gas pump, a heating element, and combinations thereof. In some embodiments, the electrical power plant comprises a distal element that is mechanically coupled to the chassis or housing.

In some embodiments, the electrical power plant comprises a heating chamber comprising a heat source. In some embodiments, the electrical power plant comprises a heating chamber comprising a heat source, wherein a gas is heated in the heating chamber before coming into contact with an oil mixture. In some embodiments, the electrical power plant comprises a heating chamber comprising a heat source, wherein a gas is heated in the heating chamber before the gas enters the reaction zone.

Combustion engine power plants are useful in a variety of design variations. In some embodiments, the engine is used to drive an alternator or generator to provide heat and gas flow via the combustion exhaust. In some embodiments, the engine is used to drive an alternator or generator to provide a gas pump and auxiliary heating via plasma or a coil while also providing heat and gas flow via the combustion exhaust. The combustion engine drives the reaction mechanism and provides at least the benefits of increased mobility and reliance on a fuel source rather than electricity.

Atomizer

Any suitable atomizer known in the art is useful to atomize the oil and deliver it into the reaction zone. In some embodiments, the atomizer comprises an atomization component selected from the group consisting of a nozzle, a port, a wick, a valve, and combinations thereof.

In some embodiments, the atomizer comprises a nozzle or a port. The nozzle or port atomizes the oil and delivers it into the reaction zone. Suitable ports known in the art, such as a Venturi port, are useful.

In some embodiments, the atomizer comprises a wick. The wick acts as a vaporizing medium. The wick delivers the oil into the reaction zone.

In some embodiments, the atomizer comprises a vaporization chamber and module to move air. In some embodiments, the module to move air is selected from the group consisting of an air pump, a fan, a turbofan, and combinations thereof.

In some embodiments, the module to move air is connected to the vaporization chamber and provides a constant airflow that evacuates vapors from the chamber.

In some embodiments, the atomizer uses superheated air to enact vaporization. In some embodiments, the atomizer comprises a pyrolyzing coil or plasma arc.

In some embodiments, the atomizer comprises a two-stage vaporization chamber. In some embodiments, air is superheated in a first stage or chamber before it comes into contact with a wick or differential pressure valve inside a secondary vaporization chamber. In some embodiments, when the atomizer comprises a differential pressure valve, a vacuum created by airflow draws the fumigant mixture into the secondary vaporization chamber, thereby obviating the need for a wick.

In some embodiments, the atomizer comprises a one-stage vaporization chamber. In some embodiments, the one-stage vaporization chamber comprises a wick that is in contact with the fumigant oil mixture and controls how much of the mixture comes in contact with the heating coil within the chamber. In some embodiments, the atomizer uses unheated air.

Control System

In some embodiments, the reactor comprises a control system. The control system controls one or more components of the reactor. In some embodiments, the control system comprises a means of control selected from the group consisting of an analog means of control, a digital means of control, and combinations thereof. In some embodiments, the control system is analog or digital. In some embodiments, the control system controls a reactor element selected from the group consisting of gas flow, power, oil feedstock, temperature, pressure, and combinations thereof.

In some embodiments, the reactor comprises a power and control module. In some embodiments, the power and control module comprises a power plant (e.g. batteries) to provide electricity and optionally electronic circuits or analog mechanisms to monitor and control various components of the reactor.

In some embodiments, the control module is in communication with a controllable component selected from the group consisting of sensors, thermostats, air pumps, heating coils, and combinations thereof. In some embodiments, the control module comprises a microprocessor. In some embodiments, the microprocessor is programmable.

In some embodiments, the control module comprises a user interface (UI). In some embodiments, the control module comprises an input output controller (10). These aspects make control of the system easier and more efficient.

Methods of Use

In many embodiments, disinfecting agents produced according to the present disclosure may be used according to any suitable means of use for such compounds.

In some embodiments, a method of using at least one disinfecting agent comprises: (i) producing the at least one disinfecting agent; and (ii) providing the at least one disinfecting agent to an application space.

In some embodiments, the providing the at least one disinfecting agent to an application space comprises providing the at least one disinfecting agent to an application space with a technique selected from the group consisting of blowing, applying, dispersing, dispensing, diffusing, distributing, and combinations thereof.

In some embodiments, the application space comprises a surface comprising a living and/or infectious target.

In some embodiments, the providing the at least one disinfecting agent to an application space comprises providing the at least one disinfecting agent to an application space with a consumer product comprising the at least one disinfecting agent.

In some embodiments, the consumer product is selected from the group consisting of a fumigant, a nebulizer, a vaporizer, mister, and combinations thereof.

EXAMPLES

Without further elaboration, it is believed that one skilled in the art using the preceding description can utilize the present disclosure to its fullest extent. The following Examples are, therefore, to be construed as merely illustrative, and not limiting of the disclosure in any way whatsoever.

Example 1

The reaction method comprises one or more method steps. Some of these steps include explicit or implied sub-steps. These steps and sub-steps are not intended to be limiting.

Disinfecting agents are mixed with one or more of propylene glycol, vegetable glycerin, glycerol, and vegetable oil. These mixed constituents are then placed in a reservoir that feeds a vaporizing mechanism. The mixture is vaporized via a wick that puts the oil mixture in contact with a heating coil, thereby vaporizing the mixture within the heating chamber. Forced air is introduced into the heating chamber, blowing the vaporized fumigant into the air. Upon settling, a protective barrier is created, due primarily to the pyrolyzed oil fraction of the mixture, which inhibits a myriad of microbial species, particularly those susceptible to distinct constituents within the fumigant. In some embodiments, the protective barrier inhibits the growth and/or proliferation of the microbial species or a living and/or infectious target.

Example 2

A heat source (e.g. a coil) heats a mixture containing an oil and a carrier. The desired temperature depends on the heat of vaporization for the mixture of disinfecting agents produced from the oil. The generally suitable range is from about 200° C. to about 550° C., with typical temperatures in the range of from about 390° C.±50° C. Next, after heating, the fumigant oil mixture is introduced into a heating chamber via a wick to bring the fumigant mixture in contact with the heated coil. Then, air flow is established through the heating chamber to disperse the volumized fumigant mixture into a space where fumigation is desired. The fumigant mixture disinfectants the exposed space and/or surfaces and deposits an antimicrobial prophylactic barrier on the surfaces. The barrier is, by most means, imperceptible as well as harmless to vertebrates, insects, and electronic devices.

Example 3

The fumigant oil mixture is produced from one or more of propylene glycol, vegetable glycerin, or vegetable oil and one or more of the disinfecting agents disclosed herein. This mixture is placed into a fumigant oil container or tank in an amount appropriate to fumigate a target space.

When the system is gravity fed or fed via capillary action (e.g. in small systems), the user waits a few moments for a wick to prime before turning on a heating coil. Once primed, and after the heating coil engaged by means of the control unit or analog switch, the airflow is turned on via the control unit or analog switch. With the introduction of an air stream, vaporized fumigant oil begins to be forced from the vaporization chamber or chambers.

When the system is large, it is fed by a fuel pump or pressure differential valve (e.g. in large systems where gravity and capillary fed systems are less appropriate), to ensure that sufficient amounts of fumigant oil are chambered to be vaporized.

TABLE 1

Exemplary representation of a reactor in accordance with the present disclosure.

| Component Number | Component |
|---|---|
| 1 | Natural disinfecting agents (e.g. antimicrobial agents) suspended in an oil or propylene glycol/vegetable glycerin (e.g. those comprising long chain fatty acids) |
| 2 | Pyrolytic nebulizer |
| 3 | Reservoir |
| 4 | Heating source (e.g. coil) |
| 5 | Reaction zone (e.g. heating chamber) |
| 6 | Wicking system |
| 7 | Air pump |
| 8 | Air stream |
| 9 | Chassis |
| 10 | One or more control systems for the air, power, and oil feeds |
| 11 | Target surface |

TABLE 2

Exemplary representation of a method in accordance with the present disclosure.

| Step Number | Step |
|---|---|
| 1 | Disinfecting agents (e.g. antimicrobial agents) are mixed with one or more of propylene glycol, vegetable glycerin, or vegetable oil |
| 2 | This mixture is added to a reservoir containing a wick and heating source (e.g. coil) |
| 3 | The mixture is vaporized by the heating source (e.g. coil) within the heating chamber |
| 4 | An air pump passes over and or through a passage in the heating chamber, blowing the vaporized mixture into the air |
| 5 | The mixture settles upon on exposed surfaces |

This written description uses examples to illustrate the present disclosure, including the best mode, and also to enable any person skilled in the art to practice the disclosure, including making and using any compositions or systems and performing any incorporated methods. The patentable scope of the disclosure is defined by the claims, and may include other examples that occur to those skilled in the art. Such other examples are intended to be within the scope of the claims if they have elements that do not differ from the literal language of the claims, or if they include equivalent elements with insubstantial differences from the literal language of the claims.

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed disclosure. The term "consisting essentially of" occupies a middle ground between "comprising" and "consisting of".

Where a disclosure or a portion thereof is defined with an open-ended term such as "comprising," it should be readily understood that (unless otherwise stated) the description should be interpreted to also describe such a disclosure using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the disclosure are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

What is claimed is:

1. A method for producing and providing at least two disinfecting agents, the method comprising:

introducing a mixture comprising an oil and a liquid carrier into a container;

transporting the mixture from the container to a reaction zone of a reactor;

reacting the oil in the reaction zone of the reactor to produce at least two disinfecting agents; and providing the at least two disinfecting agents to an application space, wherein reacting the oil in the reaction zone of the reactor to produce at least two disinfecting agents comprises reacting the oil in the reaction zone of the reactor at a temperature in the range of from about 340° C. to about 440° C., and wherein the reacting the oil in the reaction zone to produce at least two disinfecting agents comprises a pyrolytic decomposition reaction.

2. The method of claim 1, wherein transporting the mixture from the container to a reaction zone comprises atomizing the mixture.

3. The method of claim 1, wherein the providing the at least two disinfecting agents to an application space comprises providing the at least two disinfecting agents to an application space with a technique selected from the group consisting of blowing, applying, dispersing, dispensing, diffusing, distributing, and combinations thereof.

4. The method of claim 1, wherein the providing the at least two disinfecting agents to an application space comprises providing the at least two disinfecting agents to an application space with a consumer product comprising the at least two disinfecting agents.

5. The method of claim 4, wherein the consumer product is selected from the group consisting of a fumigant, a nebulizer, a vaporizer, mister, and combinations thereof.

6. The method of claim 4, wherein the liquid carrier comprises vegetable glycerin and/or glycerol.

7. The method of claim 1, wherein the application space comprises a surface comprising a living and/or infectious target.

8. The method of claim 7, wherein the providing the at least two disinfecting agents to an application space results in a protective barrier formed on the surface comprising a living and/or infectious target.

9. The method of claim 8, wherein the protective barrier inhibits the growth and/or proliferation of the living and/or infectious target.

10. The method of claim 8, wherein the protective barrier comprises the liquid carrier and is a thin film.

* * * * *